United States Patent [19]

Frazer

[11] Patent Number: Plant 7,010

[45] Date of Patent: Aug. 29, 1989

[54] DIEFFENBACHIA HYBRIDA MAUI

[75] Inventor: Edwin J. Frazer, Brisbane, Australia

[73] Assignee: Hartman Plant Laboratories, Inc., Santa Paula, Calif.

[21] Appl. No.: 23,606

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Maui, which is a seedling cross between Wilsonii and Marianne.

1 Drawing Sheet

The invention comprises a new and distinct cultivar of Dieffenbachia known as Dieffenbachia Hybride Maui.

The new cultivar is a product of a seedling cross between Dieffenbachia varieties Wilsonii and Marianne.

The following observations, measurements and values describe plants grown in Alva, Fla. under greenhouse conditions that closely approximate those generally used in horticultural practice. All color references are measured against The Royal Horticultural Society Colour Chart. Colors are approximate as color depends on horticultural practices such as light level and fertilization rate among others.

The following traits have been repeatedly observed to by characteristics which in combination distinguish Dieffenbachia Maui from other commercially available Dieffenbachia.

DISTINCTIONS:

1. Leaves are larger and wider than Camille.
2. Leaves have fewer breaks than Camille.
3. Leaves have green borders that are thinner and sharper edged than Camille.
4. Petiole clasp the stem so the leaf base stays close to the stem giving the plant a dense appearance in its interior.
5. Larger wider leaves giving the appearance of as much fullness but having more white and less green than Camille.
6. The stem as the plant matures does not elongate at the tip, bringing the upper leaves very close together.
7. The midrib is flexible enough so that the tip of the leaf can be folded back to touch its base without damaging the leaf.
8. The plant is taller than Camille.

DESCRIPTION

Propagation: Asexual production either through tissue culture or division.

Plant: In a 6 inch pot, Maui will be approximately 20 cm to 26 cm from the soil surface to the junction of the petioles of the last two unrolled leaves and approximately 40 cm to 46 cm in width after approximately 26 weeks to 36 weeks under appropriate growing conditions from tissue culture. All measurements are based on the above parameters.

Stem:

*Growth pattern.*—The stem is erect in growth and will be approximately 1.9 cm to 2.3 cm in diameter at a height of 5 cm above the soil surface.

Internode distance will be approximately 1.4 cm to 1.8 cm at a height of 3 cm above the soil.

*Color.*—The stem is striped and blotched light green and dark green.

Petiole: (based on the fourth expanded leaf from apex of the main shoot)

*Pattern.*—The petiole has fleshy edges extending from the midrib that will be referred to as wings. The wings will be approximately 8 mm to 10 mm wide 1 cm below the leaf base. The wings extend from the base of the petiole to within approximately 0.8 cm to 1.1 cm of the leaf base. The apex of the wings is emarginate. The petiole follows the stem axis but diverges from the axis approximately 1.7 cm to 2.0 cm from the leaf base forming a horizontal distance from the edge of the stem to the leaf base of approximately 0.7 cm to 1 cm.

*Physical dimensions.*—The petiole will be approximately 10 cm to 11 cm from its base to the base of the leaf. The petiole will be approximately 5 mm to 7 mm in diameter one-half way between the top of the wing to the bottom of the leaf.

*Color and color pattern.*—The petiole wings will be green (137A,B), and the midrib will be light yellow green (144D).

Leaf:

*Leaf pattern.*—The leaf will be ovate with an aristate apex and a cordate base. The margin is entire. The leaf is asymmetric with the side of the leaf unrolling first having less surface area and less undulations on the leaf margin than the side unrolling last. The leaf is oriented 10° to the stem axis at the time of full unrolling changing to 70° to the stem axis as more leaves unroll above it. The midrib droops slightly over the length of the leaf. The leaf blade droops slightly from the midrib to the margin.

*Physical dimensions.*—For the potsize and growing time indicated, the largest leaf will be approximately 28 cm to 32 cm long and approximately 13 cm to 15.5 cm wide. An average sized leaf will be approximately 21 cm to 23 cm long and approximately 10.5 cm to 12.5 cm wide. The leaf thickness is medium.

*Midrib.*—The midrib is thick and slightly greener than the surrounding leaf tissue.

*Primary veins.*—The primary veins are sunken into the adaxial side and protrud out of the abaxial side.

*Color and pattern.*—The adaxial surface of the mature, older leaf has a midrib color of 138D, becoming less green toward the apex of the leaf and a leaf blade color of 155C to 157C next to the midrib, changing abruptly to 139A within about 2–4 mm. of the edge of the leaf.

The abaxial surface of the mature, older leaf has a midrib color of 139D to 145C, being lighter at the basal-surface and changing to 143C at the surface where the leaf blade is attached thereto; the veins radiating from the midrib are 143C; the leaf blade color is 157C, changing to lighter than 144A, and becoming 137A at approximately 4–7 mm. from the leaf edge.

The adaxial surface of the newly-opened leaf has a midrib color of 157B and a leaf blade color of 1C-2D which abruptly changes to 139A approximately 1–3 mm. from the leaf edge.

The abaxial surface of the newly-opened leaf has a midrib color of 154D-145C and 145D on the basal surface, changing to 144A at the surface where the leaf blade attaches and changing to 2D toward the tip of the leaf, and a leaf blade color of 2D, changing to 137C at approximately 1–3 mm. from the leaf edge.

Axillary breaks: There will be approximately 5 to 7 axillary breaks with at least 1 leaf expanded. Leaves will show color by the third leaf and will have true color and pattern by the fourth leaf.

Inflorescences: Not present.

Roots: Thick white roots with finer laterals.

General observations: Dieffenbachia Maui is taller and broader than Camille. The leaves are larger and have a better defined green border than Camille giving a plant with whiter more formal appearance. The midribs are flexible enough that they can be doubled back without breaking. The upper leaves form a tuft of leaves giving the top of the plant a full wide appearance.

The appearance and distinctive character of Maui is shown in the FIGURE which is a true color photograph of the cultivar in an eight-inch pot.

I claim:

1. A new and distinct cultivar of Dieffenbachia as described and illustrated.

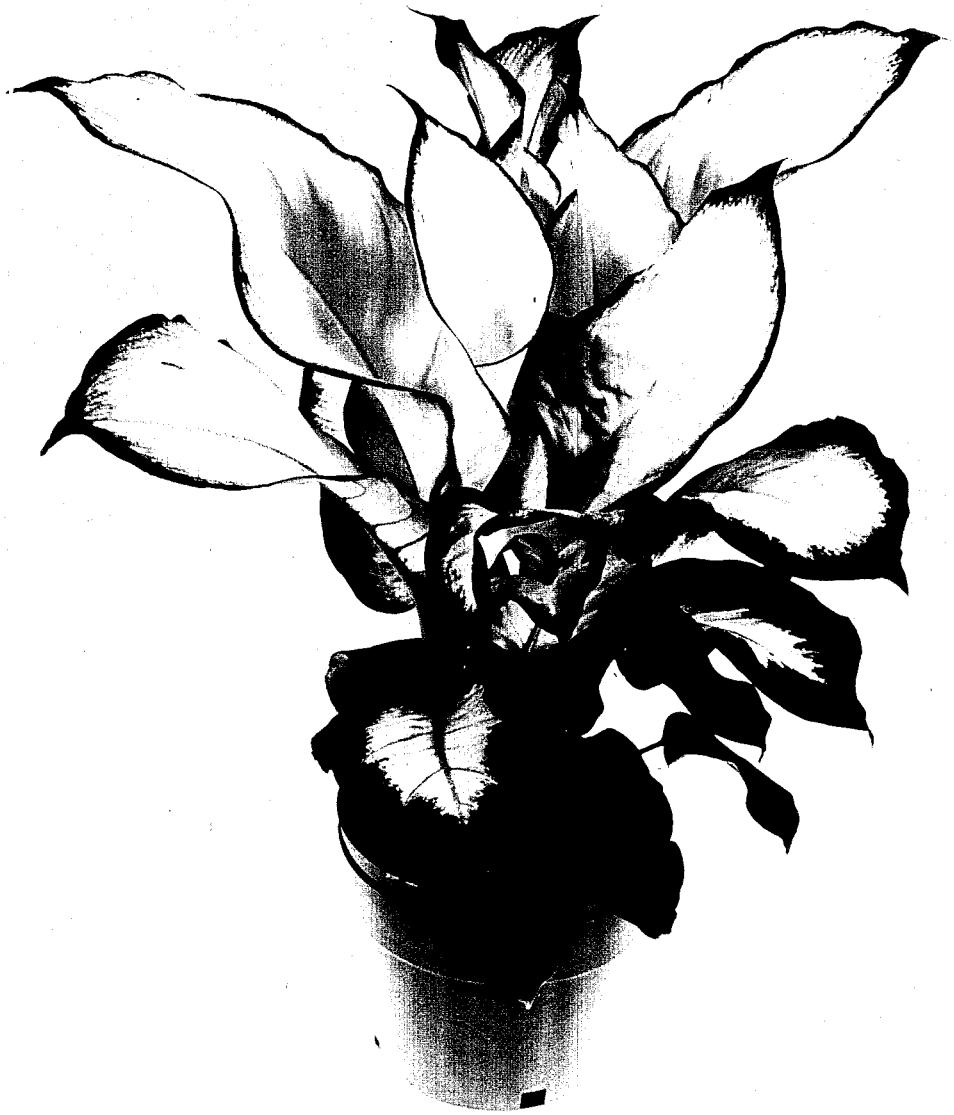

* * * * *